United States Patent
Morikane et al.

(10) Patent No.: US 6,602,592 B2
(45) Date of Patent: Aug. 5, 2003

(54) MOISTURE-RETENTIVE COOLING GEL, MOISTURE-RETENTIVE COOLING GEL LAMINATE, AND MOISTURE-RETENTIVE COOLING PLASTER

(75) Inventors: Shinji Morikane, Kashihara (JP); Daizo Morikane, Kashihara (JP)

(73) Assignee: Daiya Pharmaceutical Co., Ltd., Kashihara (JP)

( * ) Notice: Subject to any disclaimer, the term of this patent is extended or adjusted under 35 U.S.C. 154(b) by 174 days.

(21) Appl. No.: 09/876,105

(22) Filed: Jun. 8, 2001

(65) Prior Publication Data

US 2001/0036783 A1 Nov. 1, 2001

Related U.S. Application Data

(62) Division of application No. 09/301,599, filed on Apr. 29, 1999, now Pat. No. 6,335,088.

(30) Foreign Application Priority Data

Jul. 6, 1998 (JP) ............................. 10-4935
Oct. 7, 1998 (JP) ........................... 10-285164

(51) Int. Cl.$^7$ ............................... B32B 3/26
(52) U.S. Cl. ............................... 428/304.4; 428/315.5; 428/319.3; 428/297.4; 428/299.7; 424/445; 424/78.06; 442/38; 442/50; 442/394; 442/396; 514/778; 514/779; 514/781; 514/782; 514/783
(58) Field of Search ........................... 428/297.4, 299.7, 428/315.5, 304.4, 319.3; 514/778, 779, 781, 782, 783; 424/445, 78.06; 442/38, 50, 394, 396

(56) References Cited

U.S. PATENT DOCUMENTS

| | | | | |
|---|---|---|---|---|
| 4,913,755 A | * | 4/1990 | Grim | 156/145 |
| 4,964,402 A | * | 10/1990 | Grim et al. | 602/2 |
| 5,314,456 A | * | 5/1994 | Cohen | 607/109 |
| 5,388,295 A | * | 2/1995 | Sarkozi | 5/630 |
| 5,486,206 A | * | 1/1996 | Avery | 607/104 |
| 6,132,455 A | * | 10/2000 | Shang | 607/108 |
| 6,335,088 B1 | * | 1/2002 | Morikane et al. | 428/297.4 |

* cited by examiner

Primary Examiner—Terrel Morris
Assistant Examiner—Hai Vo
(74) Attorney, Agent, or Firm—Oblon, Spivak, McClelland, Maier & Neustadt, P.C.

(57) ABSTRACT

The present invention provides a moisture-retentive cooling gel, a laminate thereof, and a moisture-retentive cooling plaster, which offer moisture-retaining and cooling effects for a controlled duration and have superior functionality, e.g., capability of delivering and transporting an effective ingredient such as a pharmacological active ingredient, a perfume or a deodorant. The moisture-retentive cooling gel comprises: a water-retentive matrix (a1) of a water-soluble polymer having a water content of not lower than 40 wt %; and fibers (f) dispersed in the water-retentive matrix, the fibers (f) having a hydrophilic property at least at surfaces thereof, some of the fibers (f) being exposed on a surface of the water-retentive matrix (a1). The gel has a higher water content and a higher water vaporization rate. An endothermally water-dissolvable compound may be retained in the water-retentive matrix and/or the fibers for enhancement of the cooling capacity of the gel. The gel may be formed into a single gel layer or into a plurality of gel layers which are stacked one on another with a mesh sheet interposed therebetween for provision of the gel laminate. Further, the gel layer or the gel laminate may be provided on an air-permeable support sheet for provision of the plaster.

105 Claims, 11 Drawing Sheets

MOISTURE-RETENTIVE COOLING GEL, MOISTURE-RETENTIVE COOLING GEL LAMINATE, AND MOISTURE-RETENTIVE COOLING PLASTER

This is a division of application Ser. No. 09/301,599 filed Apr. 29, 1999. Now U.S. Pat. No. 6,335,088.

BACKGROUND OF THE INVENTION

1. Field of the Invention

The present invention relates to a moisture-retentive cooling get, a laminate thereof, and a moisture-retentive cooling plaster using such a gel or laminate.

2. Description of Related Art

Moisture-retentive cooling plasters have been known which include a support base and a gel layer such as of a water-soluble polymer provided on the support base. Such a moisture-retentive cooling plaster is superior in portability and adhesion, and used as a cooling medium for treatment of a feverish patient instead of an ice pack and an ice pillow.

The moisture-retentive cooling plaster, if its portability is an essential requirement, has a smaller water content because the size of the gel layer provided on the support base is limited. This leads to a shorter duration of moisture-retaining and cooling effects.

SUMMARY OF THE INVENTION

It is an object of the present invention to provide a moisture-retentive cooling gel, a laminate thereof, and a moisture-retentive cooling plaster, which offer moisture-retaining and cooling effects for a controlled duration and have superior functionality, e.g., capability of delivering and transporting an effective ingredient such as a pharmacological active ingredient or a perfume.

In accordance with a first aspect of the present invention, there is provided a moisture-retentive cooling gel which comprises: a water-retentive matrix of a water-soluble polymer having a water content of not lower than 40 wt %; and fibers dispersed in the water-retentive matrix, the fibers having a hydrophilic property at least at surfaces thereof, some of the fibers being exposed on a surface of the water-retentive matrix.

In accordance with a second aspect of the present invention, there is provided a moisture-retentive cooling gel laminate which comprises a plurality of layers of the aforesaid moisture-retentive cooling gel stacked one on another with a mesh sheet or a porous sheet interposed therebetween.

In accordance with a third aspect of the present invention, there is provided a moisture-retentive cooling plaster which comprises: an air-permeable support sheet; and the aforesaid moisture-retentive cooling gel or the aforesaid moisture-retentive cooling gel laminate provided on the support sheet.

The moisture-retentive cooling gel, the moisture-retentive cooling gel laminate and the moisture-retentive cooling plaster in accordance with the present invention each have a greater water content and a higher water vaporization rate and, therefore, sustainably offer superior effects when used as: (1) a medical cooling pad for cooling a part of a feverish human body; (2) a cooling package for fresh protection of fish, drinking water, liquor and the like in transportation thereof; (3) a cooling sheet for prevention of melting of chocolate in transportation thereof; (4) a pad for muscle cooling after sport and for skin care after sunburn; (5) a protective pad for water supply to a dry skin; and (6) a plaster containing an anti-inflammatory agent.

DETAILED DESCRIPTION OF THE INVENTION

Figure 1:
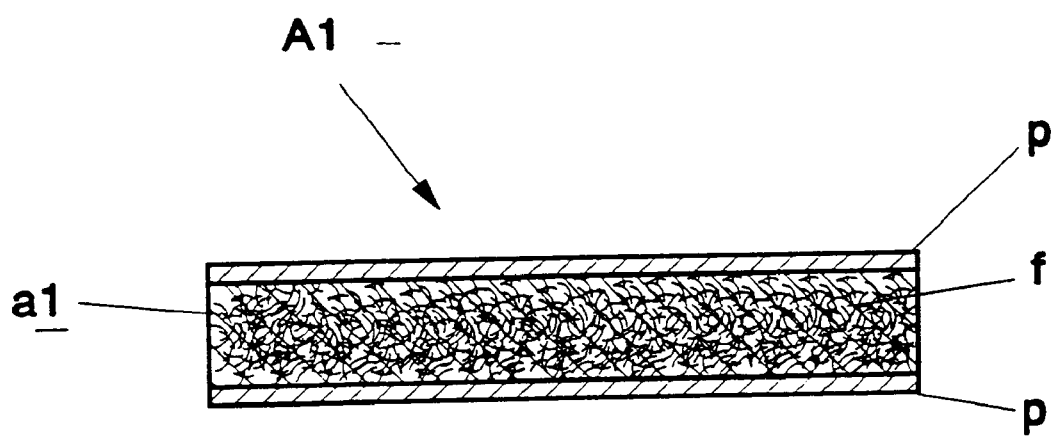
FIG. 1 is a sectional view schematically illustrating a moisture-retentive cooling gel according to Example 1 of the present invention.

In accordance with the present invention, there are provided: a moisture-retentive cooling gel (A1, A2) which comprises a water-retentive matrix of a water-soluble polymer having a water content of not lower than 40 wt %, and fibers (f) dispersed in the water-retentive matrix, the fibers having a hydrophilic property at least at surfaces thereof, at least some of the fibers being exposed on a surface of the water-retentive matrix; a moisture-retentive cooling gel (A3, A4) which comprises a water-retentive matrix of a water-soluble polymer having a water content of not lower than 40 wt %, and a water-absorbing polymer filler (v1, v11, v12, v13) dispersed in the water-retentive matrix, at least some of the water-absorbing polymer filler being exposed on a surface of the water-retentive matrix; and a moisture-retentive cooling gel (A5, A6) which comprises a water-retentive matrix of a water-soluble polymer having a water content of not lower than 40 wt %, a water-absorbing polymer filler (v1, v11, v12, v13, v2) and fibers (f) having a hydrophilic property at least at surfaces thereof, the water-absorbing polymer filler and the fibers being dispersed in the water-retentive matrix, at least some of the water-absorbing polymer filler and the fibers being exposed on a surface of the water-retentive matrix.

Examples of the fibers (f) having a hydrophilic property at least at their surfaces include pulp fibers, cotton fibers, rayon fibers, and other hydrophilic resin fibers, and hydrophobic resin fibers, glass fibers and ceramic fibers which have been surface-treated to be imparted with a hydrophilic property, but not limited thereto.

The fibers (f) are dispersed in the water-retentive matrix, preferably in such a manner that the fibers (f) are three-dimensionally entangled with each other.

The fibers (f) may preliminarily be impregnated with water and then dispersed in the water-retentive matrix. Thus, the gel to be finally obtained has a higher water content because the water retained in the fibers (f) can additionally be incorporated in the gel. This is advantageous for enhancement of the moisture-retaining and cooling effects.

Usable as the water-absorbing polymer filler (v1, v2) in the present invention are highly water-absorbing polymer fillers capable of absorbing water of a weight about 200 to 1000 times the original weight.

The water-absorbing polymer filler is preferably in a particulate or fibrous form, but the form thereof is not limited thereto. The particulate form herein includes a pellet form and a powdery form.

Where a particulate water-absorbing polymer filler (hereinafter referred to as "water-absorbing polymer particles (v1)") is used, it is preferred that the water-absorbing polymer particles (v1) are in contact with each other in the water-retentive matrix and some of the polymer particles are exposed on a surface of the water-retentive matrix.

Preferred examples of the water-absorbing polymer particles (v1) include highly water-absorbing polymer particles available under the trade names of SUNWET IM-300 and SUNWET IM-1000 from Sanyo Chemical Industry Co., Ltd., and under the trade name of AQUAKEEP from Sumitomo Seika Co., Ltd., but not limited thereto.

Usable as the fibrous water-absorbing polymer filler (hereinafter referred to as "water-absorbing polymer fibers (v2)") are highly water-absorbing and highly hygroscopic fibers such as BELL OASIS (trade name) available from Kanebo Gosen Co., Ltd.

Examples of the water-soluble polymer to be used for the water-retentive matrix in the present invention include polyacrylic acid and salts thereof, gelatin, polyvinyl alcohol, sodium carboxymethylcellulose, carrageenan, sodium alginate and carboxyvinyl polymers. These water-soluble polymers may be used alone. For enhancement of water-retentive, moisture-retentive and adhesive properties of the matrix, however, it is preferred to use a mixture of plural polymers selected from these polymers. A preferred water-soluble polymer mixture is, for example, a mixture of sodium polyacrylate, polyvinyl alcohol, gelatin and carrageenan, but not limited thereto.

Where the mixture of sodium polyacrylate, polyvinyl alcohol, gelatin and carrageenan is used as the water-soluble polymer in the present invention, for example, the blending ratio of the total weight of polyvinyl alcohol and sodium polyacrylate to the total weight of gelatin and carrageenan is preferably 1:1 to 5:1, and polyvinyl alcohol and sodium polyacrylate are typically present in a proportion of 0.1 to 25 wt %, preferably 1 to 15 wt %, more preferably 3 to 12 wt %, most preferably 5 to 10 wt %, based on the weight of the water-soluble polymer mixture. The blending weight ratio of sodium polyacrylate to polyvinyl alcohol is preferably 0.5:1 to 20:1.

In the present invention, an endothermally water-dissolvable compound may optionally be retained in the water-retentive matrix. The endothermally water-dissolvable compound may be in a solid form or in a liquid form. In view of the production process and the duration of the cooling effect, the former is more preferred.

The endothermally water-dissolvable compound is preferably contained in the water-soluble polymer forming the water-retentive matrix, but may be retained in the water-retentive matrix in any other manner. For example, the compound is retained in either or both of the fibers having a hydrophilic property at least at their surfaces and the water-absorbing polymer filler.

Examples of the endothermally water-dissolvable compound include urea and sodium nitrate, which may be used either alone or in combination.

Where the endothermally water-dissolvable compound is blended in the water-retentive matrix, the blending ratio of the compound is typically 0.1 to 25 wt %, preferably 0.5 to 20 wt %, more preferably 0.5 to 15 wt %, based on the weight of the water-retentive matrix.

In the present invention, the water-retentive matrix typically has a pH within a range between 4 and 10, preferably between 5 and 9. A pH range between 6 and 8 is more preferred because the resulting moisture-retentive cooling gel provides a cold feeling to skin and a refreshing feeling after removal of the gel.

A lower alcohol is preferably added to the water-retentive matrix to promote water vaporization for enhancement of the cooling effect and for extension of the duration of the cooling effect. Examples of the lower alcohol include methyl alcohol, ethyl alcohol and propyl alcohol, but not limited thereto. Any of alcohols which are miscible with water and have a lower boiling point than water to form an azeotrope with water may be used. Any of known humectants such as glycerol and polyethylene glycol may optionally be blended in the water-retentive matrix.

In the present invention, it is preferred to add a water-soluble pharmacological active ingredient to at least one of the water-retentive matrix and the water-absorbing polymer filler. This allows for transportation, delivery and release of the pharmacological active ingredient with water migration in the gel.

Examples of the water-soluble pharmacological active ingredient include dipotassium glycyrrhetinate, water-soluble azulene and acrinol.

In accordance with the present invention, there are also provided: a moisture-retentive cooling gel laminate (A7, A8) which comprises a mesh sheet (n1) and a plurality of layers of any of the aforesaid moisture-retentive cooling gels stacked one on another with the mesh sheet interposed therebetween; and a moisture-retentive cooling gel laminate (A9) which comprises a porous sheet (n2) and a plurality of layers of any of the aforesaid moisture-retentive cooling gels stacked one on another with the porous sheet interposed therebetween.

Usable as the mesh sheet (n1) for the gel laminate (A7, A8) of the present invention are any mesh sheets having opposite surfaces onto which the gel layers can adhere to be fixed thereon. The mesh sheet (n1) per se preferably has water-absorbing, water-retentive and water-permeable properties. Preferred examples of the mesh sheet include paper sheets, fabric sheets and relatively coarse nonwoven fabric sheets composed of hydrophilic and/or water-absorbing polymer fibers, but not limited thereto. The water-absorbing polymer fibers stated earlier as an example of the fibrous water-absorbing polymer filler (v2) are preferably used as the water-absorbing polymer fibers for the nonwoven fabric sheets.

Where the mesh sheet (n1) is composed of the polymer fibers, the mesh sheet is preferably chemically or physically surface-treated so as to be able to offer an anchoring effect to the water-retentive matrix. Thus, the gel layers can firmly be bonded and fixed onto the opposite sides of the sheet (n1) for provision of the multi-layer gel laminate.

For the chemical surface treatment, a proper surfactant, for example, may be used to impart the surfaces of the polymer fibers with a hydrophilic property. Where the sheet is subjected to the chemical surface treatment, it is preferred not to impair the water-retentive and water-permeable properties of the sheet. For the physical surface treatment, a needling process, for example, is employed to fuzz the opposite surfaces of the mesh sheet.

Preferably, the mesh sheet (n1) is preliminarily impregnated with water. Thus, the water content of the entire gel laminate is increased thereby to contribute to extension of the duration of the moisture-retaining and cooling effects.

The mesh sheet (n1) may also retain an endothermally water-dissolvable compound. This is preferred because an endothermic dissolution process occurs on interfaces between the mesh sheet and the gel layers to enhance the cooling effect. Examples of the endothermally water-dissolvable compound include those previously described.

The porous sheet (n2) to be used for the gel laminate (A9) of the present invention is composed of a flexible material. Examples thereof include open-cell foamed resin sheets, among which urethane foam sheets are preferred, but not limited thereto.

The porous sheet (n2) may also retain an endothermally water-dissolvable compound. In this case, any of the aforesaid-endothermally water-dissolvable compounds may be retained in cells of the porous sheet (n2).

In the present invention, the mesh sheet (n1) or the porous sheet (n2) retaining therein the aforesaid compound is prepared separately from the aforesaid gel layers and, when required, the gel layers are stacked on the sheet for formation of the gel laminate. This is preferred because the endothermic dissolution process can more effectively be utilized.

In accordance with the present invention, there is also provided a moisture-retentive cooling plaster (A10) which comprises an air-permeable support sheet (1), and any of the aforesaid moisture-retentive cooling gels or any of the aforesaid moisture-retentive cooling gel laminates provided on the support sheet.

In the plaster (B) of the present invention, any of air-permeable support sheets known in the art may be used on an "as is" basis as the air-permeable support sheet (1) which supports the gel or the gel laminate.

In the present invention, for ease of handling of the moisture-retentive cooling gels, the moisture-retentive cooling gel laminates and the moisture-retentive cooling plaster, at least one exposed surface thereof is preferably covered with a liner (p).

In the case of the gel of the present invention which includes the fibers (f) dispersed in the water-retentive matrix, the water contained in the water-retentive matrix easily migrates through the hydrophilic surfaces of the fibers (f) within the matrix. In addition, at least some of the fibers (f) are exposed on the surface of the water-retentive matrix, so that the water can easily be vaporized through the exposed fibers. Therefore, the rate of the water vaporization from the water-retentive matrix increases for enhancement of the cooling capacity of the gel.

In the case of the gel which includes the water-absorbing polymer filler (v1, v2) dispersed in the water-retentive matrix, the water contained in the water-retentive matrix is attracted to the water-absorbing polymer filler (v1, v2) and easily migrates through the surface and inner portions of the water-absorbing polymer filler within the matrix. In addition, at least some of the water-absorbing polymer filler (v1, v2) is exposed on the surface of the water-retentive matrix, so that the water can easily be vaporized through the exposed polymer filler. Therefore, the rate of the water vaporization from the water-retentive matrix increases for enhancement of the cooling capacity of the gel.

Further, the water absorbed by the water-absorbing polymer filler (v1, v2) is additionally incorporated in the water-retentive matrix, so that the gel has a greater water content.

In the case of the gel which includes the water-absorbing polymer filler (v1, v2) and the surface-hydrophilic fibers (f) dispersed in the water-retentive matrix, the water contained in the water-retentive matrix more easily migrates through the surface and inner portions of the water-absorbing polymer filler (v1, v2) and the hydrophilic surfaces of the fibers (f) within the matrix. In addition, at least some of the water-absorbing polymer filler (v1, v2) or the fibers (f) are exposed on the surface of the water-retentive matrix, so that the water can easily be vaporized through the exposed filler or fibers. Therefore, the rate of the water vaporization from the water-retentive matrix increases for enhancement of the cooling capacity of the gel.

Further, the water absorbed by the water-absorbing polymer filler (v1, v2) is additionally incorporated in the water-retentive matrix, so that the gel has a greater water content.

In the present invention, the fibers (f) and/or the water-absorbing polymer filler (v1, v2) dispersed in the water-retentive matrix have a good affinity for the matrix because of their surface properties, and function like reinforcement materials. Thus, the water-retentive matrix, even if having a greater volume, is free from tearing and rupture with an excellent shape retention property. Therefore, the volume of the water-retentive matrix can be increased, while the shape retention property of the matrix is ensured. Accordingly, the duration of the moisture-retaining and cooling effects of the gel can be extended by increasing the volume of the matrix.

In the case of the gel laminate of the present invention which includes a plurality of layers of the moisture-retentive cooling gel stacked one on another with the mesh sheet (n1) or the porous sheet (n2) interposed therebetween, the water content and water vaporization rate thereof can drastically be increased or properly controlled by properly determining the number of the gel layers to be used. In addition, water or an ingredient can be retained in the mesh sheet (n1) or the porous sheet (n2) so as to be incorporated in the gel laminate. Where the mesh sheet (n1) and the porous sheet (n2) are composed of a water-absorbing polymer, the water content and the amount of the ingredient to be retained therein can properly be controlled.

In the case of the gel laminate which includes the porous sheet (n2) retaining the endothermally water-dissolvable compound and the plurality of gel layers stacked one on another with the porous sheet interposed therebetween, the gel layers may be prepared separately from the porous sheet and, when the laminate is to be used, stacked one on another with the porous sheet interposed therebetween. Thus, the starting point, duration and rate of the endothermic dissolution process can be controlled as desired.

The present invention will hereinafter be described in detail by way of examples thereof. It should be understood that the invention be not limited to these examples.

EXAMPLES

Example 1

A moisture-retentive cooling gel (A1) of Example 1 was prepared in the following manner.

First, the following ingredients were blended for preparation of a water-retentive matrix of the moisture-retentive cooling gel (A1).

| | |
|---|---|
| Sodium polyacrylate | 4 g |
| Gelatin | 1 g |
| Polyvinyl alcohol | 2 g |
| Glycerol | 18 g |
| Sodium carboxymethylcellulose | 1 g |
| Carrageenan | 2 g |
| Ethyl alcohol | 1 g |
| Paraben | 0.1 g |
| Water | 70.9 g |
| | 100.0 g |

A pulp suspension was prepared in such an amount that the ratio of the pulp suspension to the water-retentive matrix was 1:10 on a dry weight basis.

The water-retentive matrix and the pulp suspension were blended in the following manner for preparation of a moisture-retentive cooling gel composition.
(1) Gelatin and carrageenan were dissolved in 20 g of water with heating.
(2) Polyvinyl alcohol was dissolved in 20 g of water with heating.
(3) The solutions obtained in the steps (1) and (2) were fully mixed with each other with stirring.
(4) Sodium polyacrylate and sodium carboxymethylcellulose were mixed with glycerol.
(5) The mixture obtained in the step (4) and the solution obtained in the step (3) were added to and mixed with the remaining ingredients with stirring, and the pulp suspension was further added to and fully mixed with the resulting mixture with stirring. Thus, the gel composition in a slurry form was prepared.

The moisture-retentive cooling gel (A1) of Example 1 which was comprised of a planar gel layer (a1) and had a sectional configuration as shown in FIG. 1 was prepared from the gel composition slurry thus prepared. More specifically, the gel composition slurry was spread in an amount of about 200 to 3000 g/m$^2$ on a polypropylene liner (p) for formation of the planar gel layer (a1), and another polypropylene liner (p) was applied onto the gel layer.

In the moisture-retentive cooling gel (A1) thus obtained, pulp fibers (f) were virtually homogeneously dispersed in the gel layer (a1), and entangled with each other to form a three-dimensional network. Some of the fibers (f) were exposed on the surfaces of the gel layer.

The moisture-retentive cooling gel (A1) in which water retained in the fibers (f) was also incorporated had a water content of about 65 to 85 wt % based on the total weight of the gel layer at maximum. Thus, the water content of the gel was remarkably increased, compared with the conventional one. Further, it was possible to form the gel composition slurry into the relatively thick planar gel layer (a1), which was strengthened by the fibers (f).

After the liner (p) was removed, the exposed surface of the planar gel layer (a1) of the moisture-retentive cooling gel (A1) had a sufficient adhesiveness to skin and the like. With the gel applied onto the skin, water easily migrated within the gel layer (a1), and easily vaporized from the gel layer at a higher water vaporization rate. This is because the fibers (f) dispersed to form a fiber network in the gel layer (a1) functioned like water channels, and some of the fibers (f) were exposed on the surface of the gel layer (a1)

The moisture-retentive cooling gel (A1) of Example 1 had a higher water content, and water channels opening to the atmosphere were formed in the gel layer (a1) by the network of the three-dimensionally entangled fibers (f). Therefore, the moisture-retaining and cooling capacities thereof were remarkably increased.

Example 2

A moisture-retentive cooling gel (A2) of Example 2 was prepared in the following manner.

First, the following ingredients were blended for preparation of a water-retentive matrix of the moisture-retentive cooling gel.

| | |
|---|---|
| Sodium polyacrylate | 6 g |
| Gelatin | 2 g |
| Polyvinyl alcohol | 3 g |
| Glycerol | 18 g |
| Sodium carboxymethylcellulose | 2 g |
| Carrageenan | 1 g |
| Ethyl alcohol | 1 g |
| Crystalline urea | 5 g |
| Water | 62 g |
| | 100 g |

A pulp suspension was prepared in such an amount that the ratio of the pulp suspension to the water-retentive matrix was 1:10 on a dry weight basis.

The water-retentive matrix and the pulp suspension were blended in the following manner for preparation of a moisture-retentive cooling gel composition.
(1) Gelatin and carrageenan were dissolved in 20 g of water with heating.
(2) Polyvinyl alcohol was dissolved in 20 g of water with heating.
(3) Sodium polyacrylate and sodium carboxymethylcellulose were mixed with glycerol.
(4) The solution obtained in the step (2) was added to and fully mixed with the solution obtained in the step (1) with stirring.
(5) The mixture obtained in the step (3) and the solution obtained in the step (4) were added to and mixed with the remaining ingredients, and the pulp suspension was further added to and fully mixed with the resulting mixture with stirring.
(6) Crystalline urea was added to the mixture obtained in the step (5) and homogeneously dispersed therein with stirring. Thus, a gel composition in a slurry form was prepared.

Figure 2:
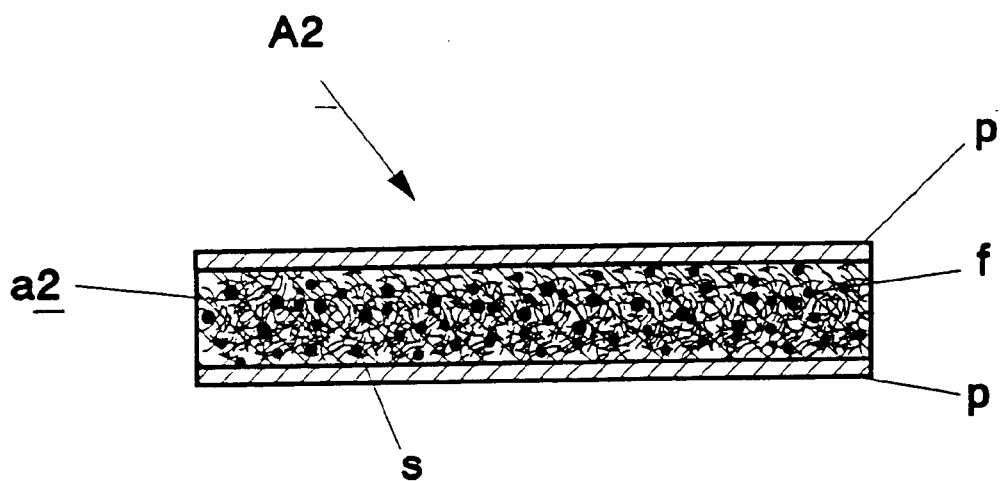
FIG. 2 is a sectional view schematically illustrating a moisture-retentive cooling gel according to Example 2 of the present invention.

The moisture-retentive cooling gel (A2) of Example 2 which included a planar gel layer (a2) and had a sectional configuration as shown in FIG. 2 was prepared in the same manner as in Example 1 from the gel composition slurry thus prepared.

The moisture-retentive cooling gel (A2) of Example 2 offered the same effects as the gel of Example 1. In addition, the gel (A2) had a higher cooling capacity because of the endothermic effect of the crystalline urea (s) retained in the water-retentive matrix.

Example 3

A moisture-retentive cooling gel of Example 3 was prepared in substantially the same manner as in Example 2, except that crystalline sodium nitrate instead of the crystalline urea was blended in the gel composition slurry so as to be dispersed in a solid form in the gel layer. It is noted that the construction of the gel of Example 3 is not shown.

The moisture-retentive cooling gel of Example 3 maintained its high cooling capacity for an extended period, because the crystalline sodium nitrate incorporated in the gel layer was gradually dissolved in the water within the gel layer to sustain the endothermic process.

Example 4

A moisture-retentive cooling gel of Example 4 was prepared in substantially the same manner as in Example 2, except that crystalline ammonium nitrate instead of the crystalline urea was blended in the gel composition slurry so as to be dispersed in a solid form in the gel layer. It is noted that the construction of the gel of Example 4 is not shown.

The moisture-retentive cooling gel of Example 4 maintained its high cooling capacity for an extended period, because the crystalline ammonium nitrate incorporated in the gel layer was gradually dissolved in the water within the gel layer to sustain the endothermic process.

Example 5

A moisture-retentive matrix of the same formulation as in Example 2 was employed for preparation of a gel composition slurry for a moisture-retentive cooling gel (A3) of Example 5.

Water-absorbing polymer pellets (AQUAKEEP available from Sumitomo Seika Co., Ltd.) were prepared, and 10 g of water was completely impregnated into 0.2 g of the water-absorbing polymer pellets (water-retentive matrix:water-absorbing polymer pellets=400:1 on a dry weight basis).

The water-retentive matrix and the water-absorbing polymer pellets impregnated with water were blended in the following manner for preparation of the moisture-retentive cooling gel composition.

(1) Gelatin was dissolved in 20 g of water with heating.
(2) Polyvinyl alcohol was dissolved in 20 g of water with heating.
(3) Sodium polyacrylate and sodium carboxymethylcellulose were mixed with glycerol.
(4) The solution obtained in the step (2) was added to and fully mixed with the solution obtained in the step (1) with stirring.
(5) The mixture obtained in the step (3) and the solution obtained in the step (4) were added to and mixed with the remaining ingredients with stirring. Then, crystalline urea and the water-absorbing polymer pellets (v1) impregnated with water were added to and fully mixed with the resulting mixture with stirring. Thus, the gel composition slurry was prepared.

Figure 3:
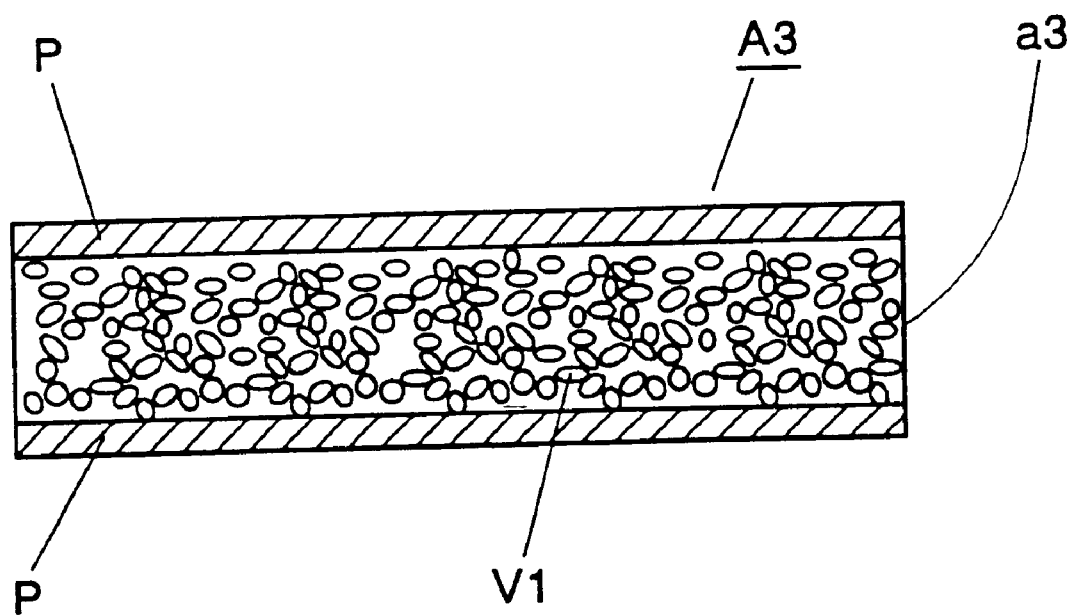
FIG. 3 is a sectional view schematically illustrating a moisture-retentive cooling gel according to Example 4 of the present invention.

The moisture-retentive cooling gel (A3) of Example 5 which included a planar gel layer (a3) and had a sectional configuration as shown in FIG. 3 was prepared in the same manner as in Example 1 from the gel composition slurry thus prepared.

As shown, the moisture-retentive cooling gel (A3) had such a structure that the water-absorbing polymer pellets (v1) were virtually in contact with one another for formation of three-dimensional linkage in the gel layer (a3) and some of the polymer pellets were exposed on surfaces of the gel layer.

The moisture-retentive cooling gel (A3) as a whole retained a far greater amount of water than the conventional one, because the water absorbed by the water-absorbing polymer pellets (v1) was added to the water contained in the water-retentive matrix.

The water-absorbing polymer pellets (v1) dispersed in the gel layer (a3) served as a reinforcement filler, so that the gel layer had a much higher strength. This permits the gel layer to have a much greater thickness.

The linkage of the water-absorbing polymer pellets (v1) in the gel layer (a3) functioned like water channels. Therefore, the water retained in the water-retentive matrix was attracted to the water-absorbing polymer pellets (v1), and vaporized through the water-absorbing polymer pellets, being released outside the gel. Thus, the water migration was promoted with a very high water vaporization rate.

Example 6

Figure 4:
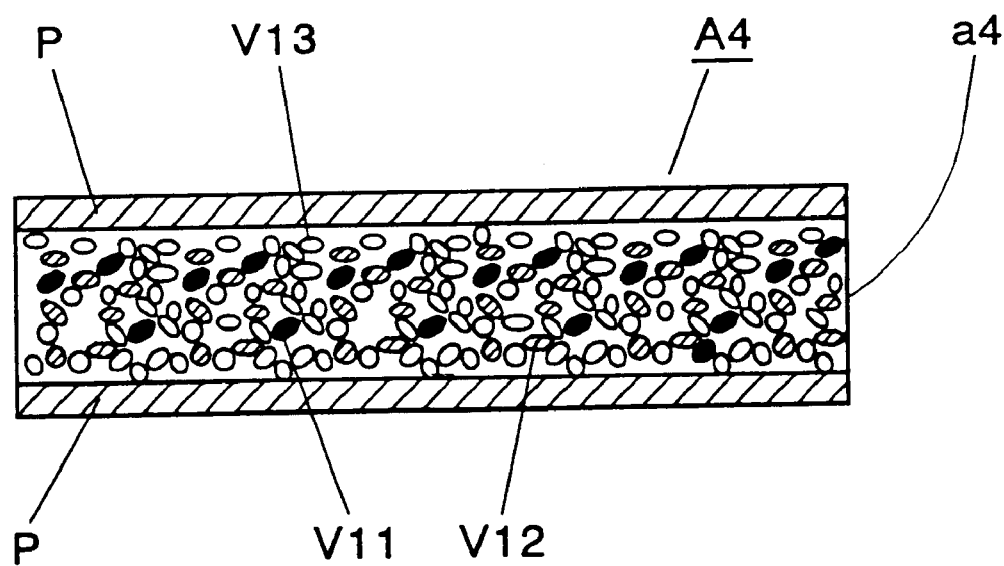
FIG. 4 is a sectional view schematically illustrating a moisture-retentive cooling gel according to Example 5 of the present invention.

A moisture-retentive cooling gel (A4) of Example 6 which included a planar gel layer (a4) and had a sectional configuration as shown in FIG. 4 was prepared in substantially the same manner as in Example 5, except that water-absorbing polymer pellets were divided into three groups (v11, v12, v13) which were distinguished by different colors (e.g., red, blue and yellow) and respectively impregnated with the following pharmacological active ingredients (i.e., three different pharmacological active ingredients).

RED No. 2, BLUE No. 1 and YELLOW No. 4 dyes were used for the color distinction of the three groups of water-absorbing polymer pellets. Then, 1% aqueous solutions of the three water-soluble pharmacological active ingredients (acrinol, water-soluble azulene and dipotassium glycyrrhetinate, hereinafter referred to simply as "pharmacological solutions") were prepared, and the water-absorbing polymer pellets (v11, v12, v13) distinguished by the three different colors were respectively impregnated with 10 g of the ingredients.

The moisture-retentive cooling gel (A4) thus obtained offered moisture-retentive and cooling effects equivalent to those offered by the gel of Example 5. In addition, the pharmacological ingredients respectively retained in the water-absorbing polymer pellets (v11, v12, v13) distinguished by the different colors were gradually released into the water-retentive matrix in the gel layer (a4), and migrate through the linkage of the water-absorbing polymer pellets (v11, v12, v13) or diffused into the gel layer toward a surface of the gel layer.

Thus, pharmacological activities were effected on the surface of the gel layer. Further, the water-absorbing polymer pellets distinguished by the plural colors made the gel layer colorful and allowed for easy confirmation of the types of the pharmacological ingredients incorporated therein.

Example 7

A moisture-retentive cooling gel of Example 7 was prepared in substantially the same manner as in Example 6, except that a perfume was used instead of one of the pharmacological solutions and impregnated into one of the three groups of water-absorbing polymer pellets distinguished by the different colors. It is noted that the construction of the gel of Example 7 is not shown.

The moisture-retentive cooling gel of Example 7 offered substantially the same effects as the gel (A4) In addition, the perfume was stably retained in the gel layer, so that the perfume and water were vaporized to waft fragrance for an extended period.

Example 8

Figure 5:
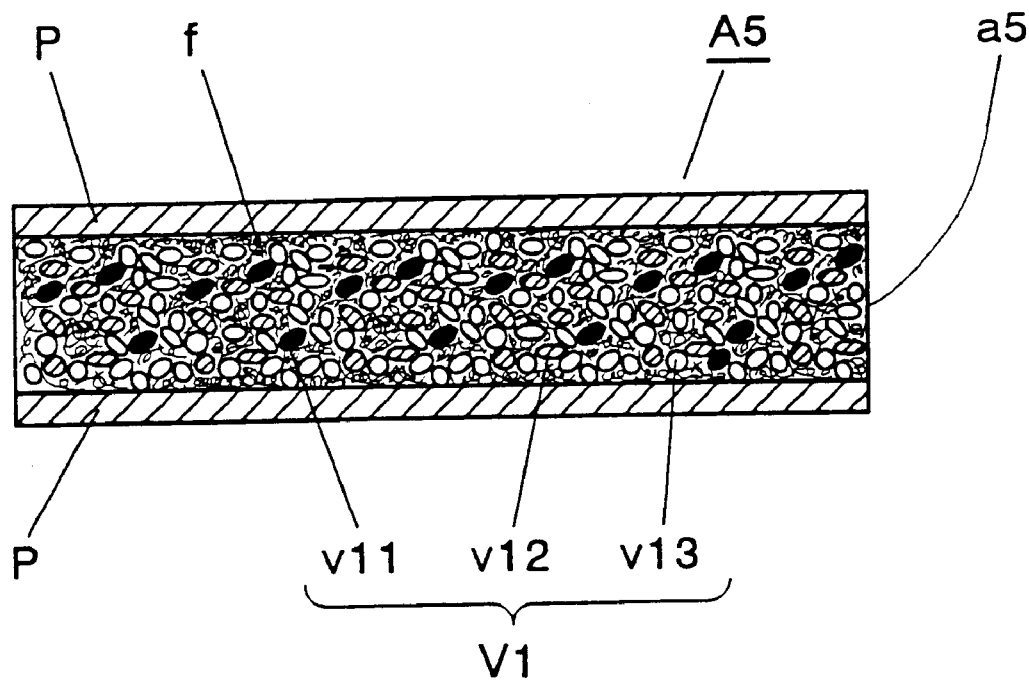
FIG. 5 is a sectional view schematically illustrating a moisture-retentive cooling gel according to Example 7 of the present invention.

For preparation of a moisture-retentive cooling gel (A5) of Example 8, a water-retentive matrix of the same formulation as in Example 5 was prepared. A pulp suspension was prepared in such an amount that the ratio of the water-retentive matrix to the pulp suspension was 10:1 on a dry weight basis, as in Example 1. Then, a gel composition slurry was prepared in the same manner as in Example 1. Three pharmacological solutions were respectively impregnated into three groups of water-absorbing polymer pellets (v11, v12, v13) distinguished by three different colors, as in Example 6. Then, the water-absorbing polymer pellets (v11, v12, v13) were mixed with the gel composition slurry. Thus, the moisture-retentive cooling gel (A5) of Example 8 which included a planar gel layer (a5) and had a sectional configuration as shown in FIG. 5 was prepared.

In the moisture-retentive cooling gel (A5) thus prepared, three-dimensional water channels were more effectively formed in the gel layer (a5) than in the moisture-retentive cooling gel (A4) of Example 6. This is because pulp fibers (f) were three-dimensionally dispersed in contact with the water-absorbing polymer pellets (v11, v12, v13) within the gel layer (a5). Therefore, the moisture-retentive cooling gel (A5) was very useful with a higher cooling capacity than the gel of Example 6 and with the capability of diffusing the pharmacological active ingredients.

Example 9

For preparation of a moisture-retentive cooling gel (A6) of Example 9, a water-retentive matrix of the same formulation as in Example 2 and a pulp suspension were prepared.

Highly water-absorbing and highly hygroscopic fibers available under the trade name of BELL OASIS from Kanebo Gosen Co., Ltd. were used as water-absorbing polymer fibers (v2). A pharmacological solution was prepared by dissolving 0.05 g of dipotassium glycyrrhetinate as a pharmacological active ingredient in 30 g of water, and then impregnated into 3 g of the water-absorbing polymer fibers (v2) (water-retentive matrix:water-absorbing polymer fibers=10:1 on a dry weight basis).

A gel composition slurry was prepared in the same manner as in Example 6 by blending the water-retentive matrix, the pulp suspension and the water-absorbing polymer fibers (v2) impregnated with the pharmacological solution.

Figure 6:
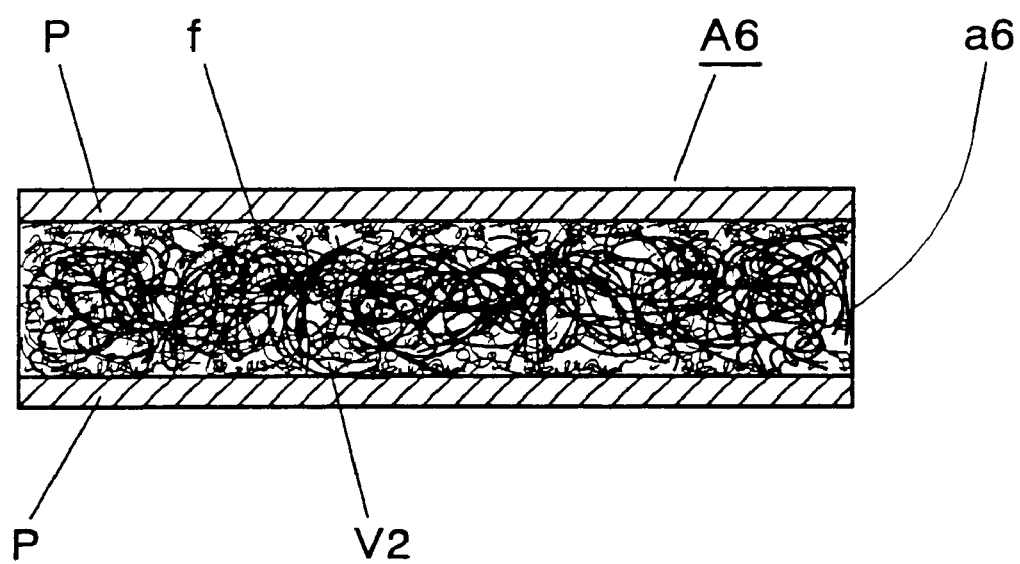
FIG. 6 is a sectional view schematically illustrating a moisture-retentive cooling gel according to Example 8 of the present invention.

The moisture-retentive cooling gel (A6) of Example 9 which included a planar gel layer (a6) and had a sectional configuration as shown in FIG. 6 was prepared in the same manner as in Example 1 from the gel composition slurry thus prepared.

Since water channels were three-dimensionally densely formed by the water-absorbing polymer fibers (v2) and pulp fibers (f) in the gel layer (a6) of the moisture-retentive cooling gel (A6), water migration in the gel layer (a6) was easier. In addition, dipotassium glycyrrhetinate impregnated in the water-absorbing polymer fibers (v2) was easily transported in the gel layer (a6) by the water migration thereby to be efficiently delivered to an intended surface of the gel layer.

Example 10

Figure 7:
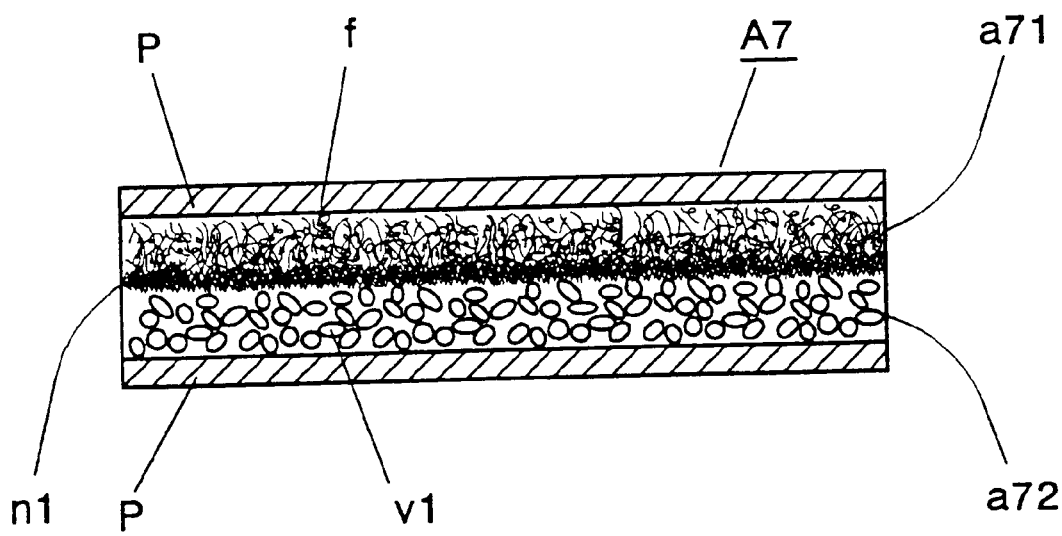
FIG. 7 is a sectional view schematically illustrating a moisture-retentive cooling gel laminate according to Example 9 of the present invention.

A moisture-retentive cooling gel laminate (A7) of Example 10 which has a sectional configuration as shown in FIG. 7 has a two-layer structure including a first gel layer (a71) and a second gel layer (a72) which are stacked one on the other with a mesh sheet (n1) interposed therebetween, and held between upper and lower polypropylene liners (p, p).

The first gel layer (a71) is composed of a gel composition slurry of the same formulation as in Example 1, and the second gel layer (a72) is composed of a gel composition slurry of the same formulation as in Example 5.

The mesh sheet (n1) is a water-permeable and hydrophilic coarse nonwoven fabric composed of polyester fibers and rayon fibers blended in a ratio of 1:1 and entangled with each other. The mesh sheet (n1) is preliminarily subjected to a needling process so that opposite surfaces thereof are fuzzed.

In the two-layered moisture-retentive cooling gel laminate (A7), water channels are formed in the first gel layer (a71) by pulp fibers. In the second gel layer (a72), water channels are formed by water-absorbing polymer pellets in contact with each other, and a greater amount of water retained in the water-absorbing polymer pellets is incorporated.

In addition, the first and second gel layers (a71, a72) are firmly bonded to the water-permeable and hydrophilic mesh sheet (n1) with some fibers of the fuzzed mesh sheet (n1) protruding into the respective gel layers. Water channels are also formed by these fibers.

Thus, the moisture-retentive cooling gel laminate (A7) has a higher water content and a higher water vaporization rate thereby to maintain a high cooling capacity for a long period.

Example 11

A moisture-retentive cooling gel laminate of Example 11 has substantially the same construction as the gel laminate of Example 10, except that the following mesh sheet is employed.

The mesh sheet employed in Example 11 is composed of highly water-absorbing and hygroscopic polymer fibers available under the trade name of BELL OASIS which were employed in Example 9.

The gel laminate offers more excellent effects than the gel laminate of Example 10. This is because a greater amount of water absorbed by the mesh sheet is incorporated in the gel laminate, and the mesh sheet provides water channels between the gel layers of the laminate to allow for water vaporization and water communication therethrough.

Example 12

Figure 8:
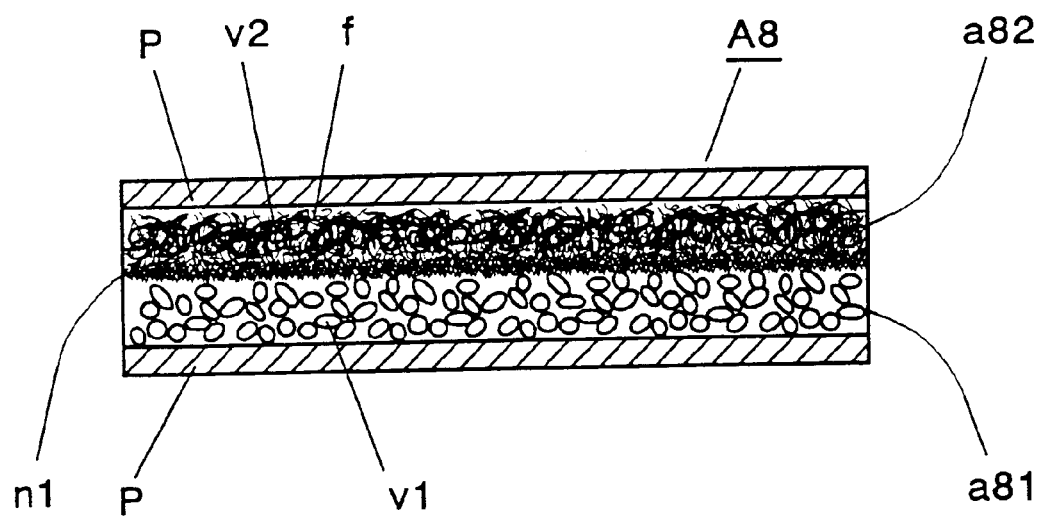
FIG. 8 is a sectional view schematically illustrating a moisture-retentive cooling gel laminate according to Example 11 of the present invention.

A moisture-retentive cooling gel laminate (A8) of Example 12 has a sectional configuration as shown in FIG. 8, and includes a first gel layer (a81) and a second gel layer (a82) which are stacked one on the other with a mesh sheet (n1) interposed therebetween and held between upper and lower polypropylene liners (p, p).

The first gel layer (a81) is composed of a gel composition slurry of the same formulation as in Example 5, and the second gel layer (a82) is composed of a gel composition slurry of the same formulation as in Example 9. The mesh sheet (n1) is the same as that employed in Example 10, and is preliminarily subjected to a needling process so that opposite surfaces thereof are fuzzed.

In the two-layered moisture-retentive cooling gel laminate (A8), water channels are formed in the first gel layer (a81) by the water-absorbing polymer pellets (v1) in contact with each other, and a greater amount of water retained in the polymer pellets (v1) is incorporated in the first gel layer (a81). In the second gel layer (a82), a greater amount of water retained in the water-absorbing polymer fibers (v2) is incorporated, and water channels are formed by the water-absorbing polymer fibers (v2). In addition, the first and second gel layers (a81, a82) are firmly bonded to the water-permeable and hydrophilic mesh sheet (n1) with some fibers of the fuzzed mesh sheet (n1) protruding into the respective gel layers.

With this arrangement, the water content is drastically increased, and the water vaporization rate is increased by the formation of the water channels in the gel layers. Therefore, the moisture-retentive cooling gel laminate (A8) can maintain a high cooling capacity for an extended period.

Example 13

Figure 9:
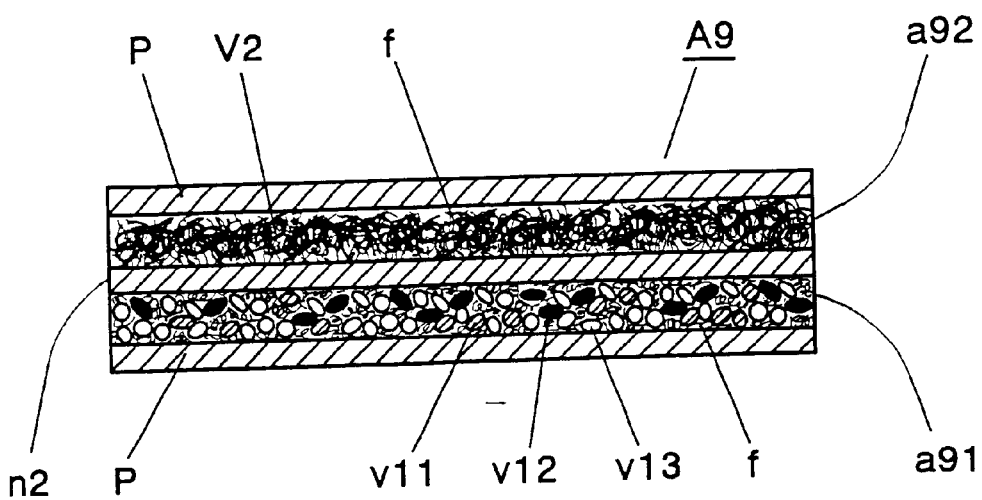
FIG. 9 is a sectional view schematically illustrating a moisture-retentive cooling gel laminate according to Example 12 of the present invention.

A moisture-retentive cooling gel laminate (A9) of Example 13 has a sectional configuration as shown in FIG. 9, and includes a first gel layer (a91) and a second gel layer (a92) which are stacked one on the other with a porous sheet (n2) interposed therebetween.

The first gel layer (a91) is prepared in the same manner as in Example 6 by employing a gel composition slurry of the same formulation as in Example 1 and three groups of water-absorbing polymer pellets (v11, v12, v13) distinguished by three different colors and respectively impregnated with pharmacological solutions as in Example 6.

The second gel layer (a92) is prepared in the same manner as in Example 9 by employing a gel composition slurry of the same formulation as in Example 1 and water-absorbing polymer fibers (v2) as employed in Example 9.

The porous sheet (n2) is a polyurethane foam sheet containing open cells, in which crystalline sodium nitrate not shown are contained.

Figure 10:
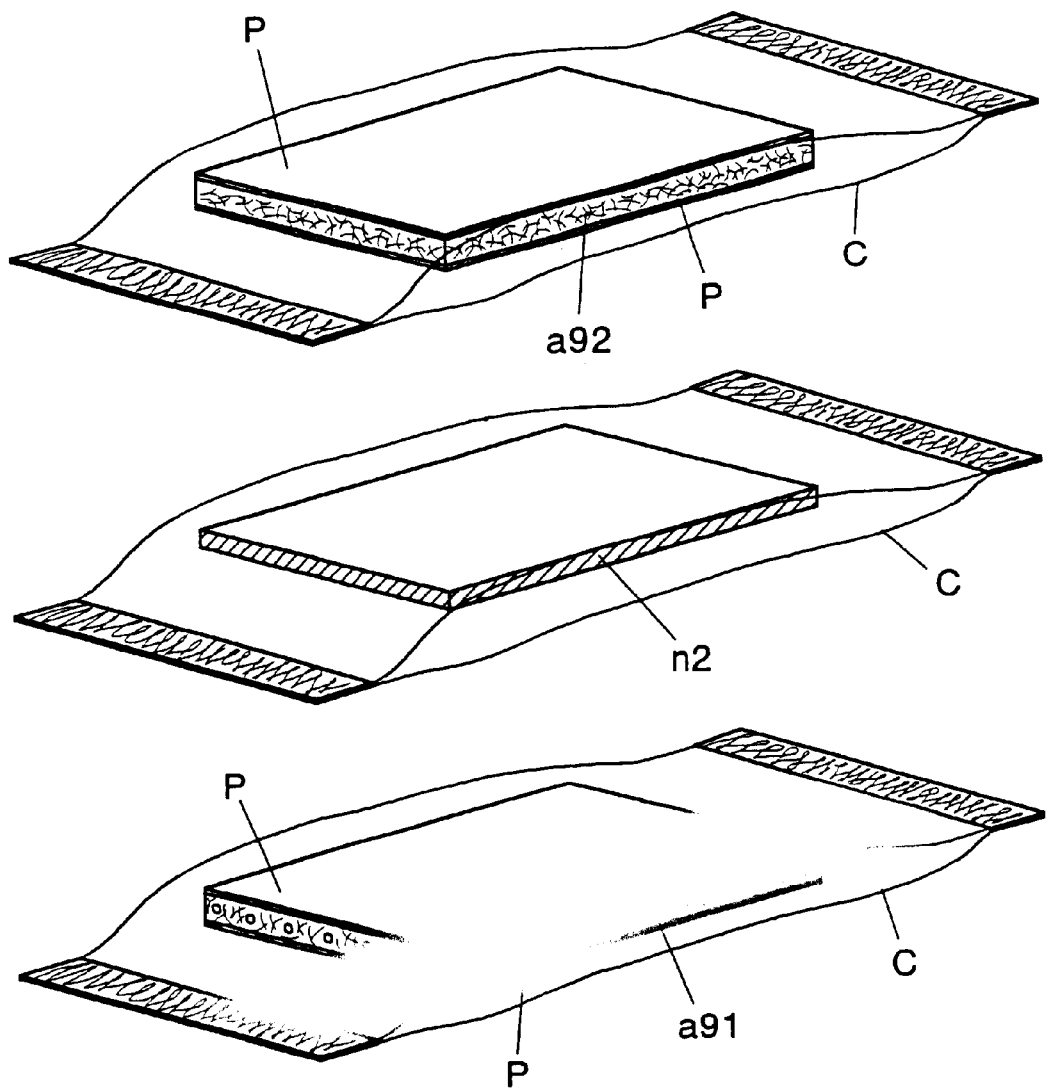
FIG. 10 is a perspective view illustrating separately packaged compounds of the gel laminate of FIG. 9.

The first gel layer (a91) and the second gel layer (a92) which are each held between polypropylene liners (p, p), and the porous sheet (n2) retaining sodium nitrate are individually enclosed in moisture-impermeable film bags (c) in a moisture free state as shown in FIG. 10.

The first and second gel layers (a91, a92) and the porous sheet (n2) thus individually enclosed are taken out of the film bags (c) when required. Then, the first gel layer (a91) and the second gel layer (a92) with one-side liners (p, p) removed therefrom are respectively bonded onto upper and lower surfaces of the porous sheet (n2), and pressed against the porous sheet (n2) from the other-side liners (p, p) by fingers, so that surface portions thereof are squeezed into the porous sheet (n2). Thus, the gel laminate (A9) having the construction shown in FIG. 9 is obtained.

As described above, the gel laminate (A9) can easily be produced, when needed, by combining the first and second gel layers (a91, a92) with the porous sheet (n2). In the gel laminate (A9) thus produced, the crystalline sodium nitrate retained in the porous sheet (n2) is dissolved in water contained in the water-retentive matrix immediately after being brought into contact with the water-retentive matrix squeezed into cells of the porous sheet (n2), thereby starting the endothermic process to enhance the cooling effect.

The gel laminate (A9) can be produced in situ when needed, so that the endothermic process of dissolution of the crystalline sodium nitrate can be started at the use of the gel laminate. Therefore, the endothermic process can effectively be utilized for a long period. In addition, the first gel layer (a91) and the second gel layer (a92) offer the same effects as the gel layers of the examples described above.

Example 14

A moisture-retentive cooling gel laminate of Example 14 has substantially the same construction as the gel laminate of Example 13, except that a mesh sheet composed of pulp fibers is used instead of the porous sheet. In is noted that the construction of the gel laminate of Example 14 is not shown.

In the gel laminate of Example 14, crystalline sodium nitrate is retained in the mesh sheet composed of the pulp fibers. Therefore, when the first and second gel layers are bonded on opposite surfaces of the mesh sheet, water retained in the respective gel layers is introduced into the sheet through the pulp fibers, so that the endothermic-process is promptly started over the entire sheet. Thus, a greater cooling effect can promptly be obtained.

Example 15

A moisture-retentive cooling plaster can be obtained by providing any of the moisture-retentive cooling gels of Examples 1 to 9 or any of the moisture-retentive cooling gel laminates of Examples 10 to 14 on an air-permeable support sheet.

Figure 11:
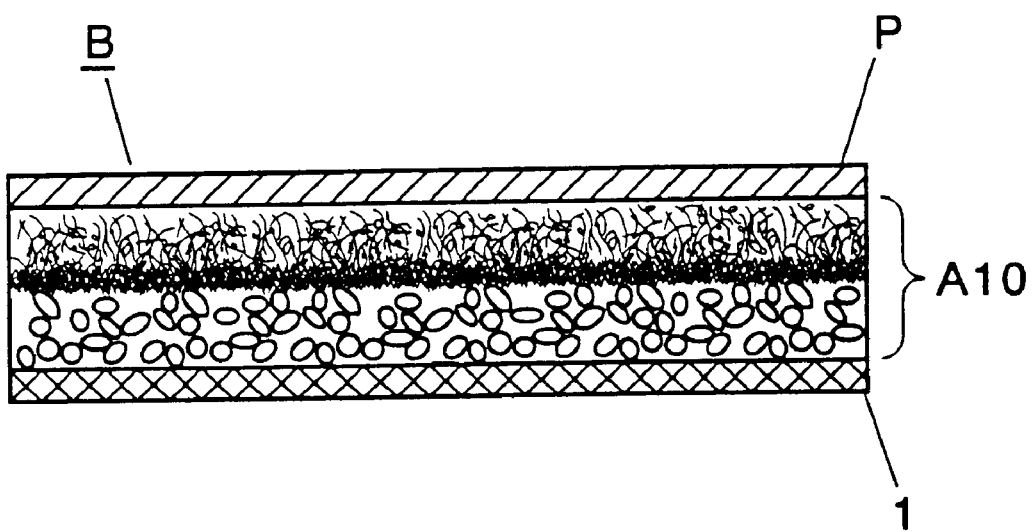
FIG. 11 is a sectional view schematically illustrating a moisture-retentive cooling plaster according to Example 14 of the present invention.

A moisture-retentive cooling plaster (B) employing the gel laminate of Example 12 is shown in FIG. 11 as one typical example. In FIG. 11, there are shown the air-permeable support sheet (1), the moisture-retentive cooling gel laminate (A10) and a propylene liner (p).

The air-permeable support sheet (1) is, for example, an open cell polyester-urethane foam sheet having a thickness of 1.5 mm, a cell number of 13±3 cells/25 mm, a tensile strength of not lower than 0.7 kg/cm, an extensibility of not lower than 100% and a density of 30±5 kg/m$^2$.

Such a plaster advantageously enjoys the effects offered by the gel laminate as well as effects offered by the support sheet. More specifically, the plaster is highly flexible and does not burden a surface on which the plaster is applied. In addition, the support sheet of the plaster is excellent in printability, so that an illustration, a trade mark and letters can clearly be printed on the support sheet.

As can be understood from the examples described above, the moisture-retentive cooling gels according to the present invention each have a higher moisture-retention capacity because the water-retentive matrix is capable of retaining a greater amount of water.

Where the fibers are dispersed in the water-retentive matrix, the fibers ensure easy water migration within the matrix and easy water vaporization from the matrix, thereby ensuring a higher cooling capacity.

Further, the fibers dispersed in the water-retentive matrix have a good affinity for the matrix because of the hydrophilic property imparted to the surfaces of the fibers, and function like a reinforcement material. Therefore, the water-retentive matrix has a superior shape-retention property, so that the volume of the water-retentive matrix can be increased. This allows the gels to retain a greater amount of water, making the moisture-retaining and cooling effects thereof sustainable.

Where the water-absorbing polymer filler (particles or fibers) is dispersed in the water-retentive matrix, the water content of the water-retentive matrix is remarkably increased, and water channels are formed in the water-retentive matrix by the linkage of the water-absorbing polymer particles or fibers. This increases the water migration rate and the water vaporization amount, thereby increasing the cooling capacity.

Moreover, a water-soluble pharmacological active ingredient retained in the water-absorbing polymer filler can be incorporated in the water-retentive matrix, and transported within the matrix. Further, a plurality of pharmacological active ingredients and/or a perfume and/or a deodorant can be retained in plural groups of water-absorbing polymer particles distinguished by different colors. Thus, the gels are made more functional.

The water channels are stably formed by the water-absorbing polymer filler in the water-retentive matrix, thereby remarkably improving the capacity for transporting the pharmacological active ingredients, a perfume, a deodorant and water.

Further, the liners provided on the gels ensure easy handling.

In the moisture-retentive cooling gel laminate according to the present invention, the plurality of gel layers are stacked one on another with the mesh sheet or the porous sheet interposed therebetween, so that the total thickness of the gel layers can be increased. Therefore, the water content can be increased to improve the cooling capacity and the moisture-retention capacity. Further, the water content of the gel laminate can drastically be increased by increasing the number of the gel layers, so that the duration of the moisture-retaining and cooling effects can remarkably be extended. Moreover, the addition of the endothermally water-dissolvable compound further improves the cooling capacity.

Where the mesh sheet is composed of the water-absorbing polymer fibers, the water content can be increased, and active ingredients such as a water-soluble pharmacological active ingredient, a perfume or a deodorant can be retained in the mesh sheet. Thus, the gel laminate has multiple functions.

Further, the gel laminate can be produced when needed by combining the gel layers with the mesh or porous sheet retaining the endothermally water-dissolvable compound, so that the endothermic process can be started upon production of the gel laminate. Thus, the endothermic process can effectively be utilized. In addition, the gel laminate has a good portability.

While the present invention has thus been described in detail with reference to specific examples thereof, it should be understood that these examples be not limitative of the invention. Various modifications may be made without departing from the spirit and scope of the invention as defined in the appended claims.

What is claimed is:

1. A moisture-retentive cooling gel laminate comprising a porous sheet and a plurality of layers of a moisture-retentive cooling gel, said cooling gel comprising: a water-retentive matrix of a water-soluble polymer, the matrix having a water content of not lower than 40 wt %; and fibers dispersed in the water-retentive matrix, the fibers having a hydrophilic property at least at surfaces thereof, at least some of the fibers being exposed on a surface of the water-retentive matrix, the plurality of gel layers being stacked one on another with the mesh sheet interposed therebetween.

2. A moisture-retentive cooling gel laminate as set forth in claim 1, wherein the mesh sheet contains an endothermally water-dissolvable compound.

3. A moisture-retentive cooling gel laminate as set forth in claim 1, wherein the mesh sheet consists of a fibrous water-absorbing polymer.

4. A moisture-retentive cooling gel laminate as set forth in claim 1, wherein the water-absorbing polymer filler contains at least one compound selected from the group consisting of a water-soluble pharmacological active ingredient, a perfume and a deodorant.

5. A moisture-retentive cooling gel laminate as set forth in claim 1, which is formed into a planer layer having opposite surfaces on at least one of which is covered with a liner.

6. A moisture-retentive cooling plaster comprising a moisture-retentive cooling gel laminate as recited in claim 1 and an air-permeable support sheet, the moisture-retentive cooling gel laminate being supported on the support sheet.

7. A moisture-retentive cooling plaster as set forth in claim 6, wherein the air-permeable support sheet contains an endothermally water-dissolvable compound.

8. A moisture-retentive cooling plaster as set forth in claim 6, wherein the laminate is formed into a planer layer having opposite surfaces on at least one of which is covered with a liner.

9. A moisture-retentive cooling gel laminate comprising a mesh sheet, a layer of a moisture-retentive cooling gel, said cooling gel comprising: a water-retentive matrix of a water-soluble polymer, the matrix having a water content of not lower than 40 wt %; and fibers dispersed in the water-retentive matrix, the fibers having a hydrophilic property at least at surfaces thereof, at least some of the fibers being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the mesh sheet interposed therebetween.

10. A moisture-retentive cooling gel laminate as set forth in claim 9, wherein the mesh sheet contains an endothermally water-dissolvable compound.

11. A moisture-retentive cooling gel laminate as set forth in claim 9, wherein the mesh sheet consists of a fibrous water-absorbing polymer.

12. A moisture-retentive cooling gel laminate as set forth in claim 9, wherein the water-absorbing polymer filler contains at least one compound selected from the group consisting of a water-soluble pharmacological active ingredient, a perfume and a deodorant.

13. A moisture-retentive cooling gel laminate as set forth in claim 9, which is formed into a planer layer having opposite surfaces on at least one of which is covered with a liner.

14. A moisture-retentive cooling plaster comprising a moisture-retentive cooling gel laminate as recited in claim 9 and an air-permeable support sheet, the moisture-retentive cooling gel laminate being supported on the support sheet.

15. A moisture-retentive cooling plaster as set forth in claim 14, wherein the air-permeable support sheet contains an endothermally water-dissolvable compound.

16. A moisture-retentive cooling plaster as set forth in claim 14, wherein the laminate is formed into a planer layer having opposite surfaces on at least one of which is covered with a liner.

17. A moisture-retentive cooling gel laminate comprising a porous sheet and a plurality of layers of a moisture-retentive cooling gel, said cooling gel comprising: a water-retentive matrix of a water-soluble polymer, the matrix having a water content of not lower than 40 wt %; and fibers dispersed in the water-retentive matrix, the fibers having a hydrophilic property at least at surfaces thereof, at least some of the fibers being exposed on a surface of the water-retentive matrix; the plurality of gel layers being stacked one on another with the porous sheet interposed therebetween.

18. A moisture-retentive cooling gel laminate as set forth in claim 17, wherein the porous sheet contains an endothermally water-dissolvable compound.

19. A moisture-retentive cooling gel laminate as set forth in claim 17, wherein the porous sheet consists of a polyurethane foam sheet containing open cells.

20. A moisture-retentive cooling gel laminate as set forth in claim 17, wherein the water-absorbing polymer filler contains at least one compound selected from the group consisting of a water-soluble pharmacological active ingredient, a perfume and a deodorant.

21. A moisture-retentive cooling gel laminate as set forth in claim 17, which is formed into a planer layer having opposite surfaces on at least one of which is covered with a liner.

22. A moisture-retentive cooling plaster comprising a moisture-retentive cooling gel laminate as recited in claim 17 and an air-permeable support sheet, the moisture-retentive cooling gel laminate being supported on the support sheet.

23. A moisture-retentive cooling plaster as set forth in claim 22, wherein the air-permeable support sheet contains an endothermally water-dissolvable compound.

24. A moisture-retentive cooling plaster as set forth in claim 22, wherein the laminate is formed into a planer layer having opposite surfaces on at least one of which is covered with a liner.

25. A moisture-retentive cooling gel laminate comprising a porous sheet, a layer of a moisture-retentive cooling gel, said cooling gel comprising: a water-retentive matrix of a water-soluble polymer, the matrix having a water content of not lower than 40 wt %; and fibers dispersed in the water-retentive matrix, the fibers having a hydrophilic property at least at surfaces thereof, at least some of the fibers being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the porous sheet interposed therebetween.

26. A moisture-retentive cooling gel laminate as set forth in claim 25, wherein the porous sheet contains an endothermally water-dissolvable compound.

27. A moisture-retentive cooling gel laminate as set forth in claim 25, wherein the porous sheet consists of a polyurethane foam sheet containing open cells.

28. A moisture-retentive cooling gel laminate as set-forth in claim 25, wherein the water-absorbing polymer filler contains at least one compound selected from the group consisting of a water-soluble pharmacological active ingredient, a perfume and a deodorant.

29. A moisture-retentive cooling gel laminate as set forth in claim 25, which is formed into a planer layer having opposite surfaces on at least one of which is covered with a liner.

30. A moisture-retentive cooling plaster comprising a moisture-retentive cooling gel laminate as recited in claim 25 and an air-permeable support sheet, the moisture-retentive cooling gel laminate being supported on the support sheet.

31. A moisture-retentive cooling plaster as set forth in claim 30, wherein the air-permeable support sheet contains an endothermally water-dissolvable compound.

32. A moisture-retentive cooling plaster as set forth in claim 31, wherein the laminate is formed into a planer layer having opposite surfaces on at least one of which is covered with a liner.

33. A moisture-retentive cooling plaster comprising a moisture-retentive cooling gel, said cooling gel comprising: a water-retentive matrix of a water-soluble polymer, the matrix having a water content of not lower than 40 wt %; and fibers dispersed in the water-retentive matrix, the fibers having a hydrophilic property at least at surfaces thereof, at least some of the fibers being exposed on a surface of the water-retentive matrix; and an air-permeable support sheet, the moisture-retentive cooling gel being supported on the support sheet.

34. A moisture-retentive cooling plaster as set forth in claim 33, wherein the air-permeable support sheet contains an endothermally water-dissolvable compound.

35. A moisture-retentive cooling plaster as set forth in claim 33, wherein the gel is formed into a planer layer having opposite surfaces on at least one of which is covered with a liner.

36. A moisture-retentive cooling gel laminate comprising a mesh sheet and a plurality of layers of a moisture-retentive cooling gel, said cooling gel comprising: a water-retentive matrix of a water-soluble polymer, said matrix having a water content of not lower than 40 wt %; and a water-absorbing polymer filler dispersed in the water-retentive matrix; at least one of the water-absorbing polymer filler being exposed on a surface of the water-retentive matrix; the plurality of gel layers being stacked one on another with the mesh sheet interposed therebetween.

37. A moisture-retentive cooling gel laminate as set forth in claim 36, wherein the mesh sheet contains an endothermally water-dissolvable compound.

38. A moisture-retentive cooling gel laminate as set forth in claim 36, wherein the mesh sheet consists of a fibrous water-absorbing polymer.

39. A moisture-retentive cooling gel laminate as set forth in claim 36, wherein the water-absorbing polymer filler contains at least one compound selected from the group consisting of a water-soluble pharmacological active ingredient, a perfume and a deodorant.

40. A moisture-retentive cooling gel laminate as set forth in claim 36, which is formed into a planer layer having opposite surfaces on at least one of which is covered with a liner.

41. A moisture-retentive cooling plaster comprising a moisture-retentive cooling gel laminate as recited in claim 36, and an air-permeable support sheet, the moisture-retentive cooling gel laminate being supported on the support sheet.

42. A moisture-retentive cooling plaster as set forth in claim 41, wherein the air-permeable support sheet contains an endothermally water-dissolvable compound.

43. A moisture-retentive cooling plaster as set forth in claim 41, wherein the laminate is formed into a planer layer having opposite surfaces on at least one of which is covered with a liner.

44. A moisture-retentive cooling gel laminate comprising a mesh sheet, a layer of a moisture-retentive cooling gel, said cooling gel comprising: a water-retentive matrix of a water-soluble polymer, said matrix having a water content of not lower than 40 wt %; and a water-absorbing polymer filler dispersed in the water-retentive matrix, at least one of the water-absorbing polymer filler being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the mesh sheet interposed therebetween.

45. A moisture-retentive cooling gel laminate as set forth in claim 44, wherein the mesh sheet contains an endothermally water-dissolvable compound.

46. A moisture-retentive cooling gel laminate as set forth in claim 44, wherein the mesh sheet consists of a fibrous water-absorbing polymer.

47. A moisture-retentive cooling gel laminate as set forth in claim 44, wherein the water-absorbing polymer filler contains at least one compound selected from the group consisting of a water-soluble pharmacological active ingredient, a perfume and a deodorant.

48. A moisture-retentive cooling gel laminate as set forth in claim 44, which is formed into a planer layer having opposite surfaces on at least one of which is covered with a liner.

49. A moisture-retentive cooling plaster comprising a moisture-retentive cooling gel laminate as recited in claim 44, and air-permeable support sheet, the moisture-retentive cooling gel laminate being supported on the support sheet.

50. A moisture-retentive cooling plaster as set forth in claim 49, wherein the air-permeable support sheet contains an endothermally water-dissolvable compound.

51. A moisture-retentive cooling plaster as set forth in claim 49, wherein the laminate is formed into a planer layer having opposite surfaces on at least one of which is covered with a liner.

52. A moisture-retentive cooling gel laminate comprising a porous sheet a plurality of layers of a moisture-retentive cooling gel, said cooling gel comprising: a water-retentive matrix of a water-soluble polymer, said matrix having a water content of not lower than 40 wt %; and a water-absorbing polymer filler dispersed in the water-retentive matrix, at least one of the water-absorbing polymer filler being exposed on a surface of the water-retentive matrix, the plurality of gel layers being stacked one on another with the porous sheet interposed therebetween.

53. A moisture-retentive cooling gel laminate as set forth in claim 52, wherein the porous sheet contains an endothermally water-dissolvable compound.

54. A moisture-retentive cooling gel laminate as set forth in claim 52, wherein the porous sheet consists of a polyurethane foam sheet containing open cells.

55. A moisture-retentive cooling gel laminate as set forth in claim 52, wherein the water-absorbing polymer filler contains at least one compound selected from the group consisting of a water-soluble pharmacological active ingredient, a perfume and a deodorant.

56. A moisture-retentive cooling gel laminate as set forth in claim 52, which is formed into a planer layer having opposite surfaces on at least one of which is covered with a liner.

57. A moisture-retentive cooling gel laminate as set forth in claim 52, which is formed into a planer layer having opposite surfaces on at least one of which is covered with a liner.

58. A moisture-retentive cooling plaster comprising a moisture-retentive cooling gel laminate as recited in claim 52 and an air-permeable support sheet, the moisture-retentive cooling gel laminate being supported on the support sheet.

59. A moisture-retentive cooling plaster as set forth in claim 58, wherein the air-permeable support sheet contains an endothermally water-dissolvable compound.

60. A moisture-retentive cooling plaster as set forth in claim 58, wherein the laminate is formed into a planer layer having opposite surfaces on at least one of which is covered with a liner.

61. A moisture-retentive cooling gel laminate comprising a porous sheet, a layer of a moisture-retentive cooling gel, said cooling gel comprising: a water-retentive matrix of a water-soluble polymer, said matrix having a water content of not lower than 40 wt %; and a water-absorbing polymer filler dispersed in the water-retentive matrix, at least one of the water-absorbing polymer filler being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the porous sheet interposed therebetween.

62. A moisture-retentive cooling gel laminate as set forth in claim 61, wherein the porous sheet contains an endothermally water-dissolvable compound.

63. A moisture-retentive cooling gel laminate as set forth in claim 61, wherein the porous sheet consists of a polyurethane foam sheet containing open cells.

64. A moisture-retentive cooling gel laminate as set forth in claim 61, wherein the water-absorbing polymer filler contains at least one compound selected from the group consisting of a water-soluble pharmacological active ingredient, a perfume and a deodorant.

65. A moisture-retentive cooling plaster comprising a moisture-retentive cooling gel laminate as recited in claim 61 and an air-permeable support sheet, the moisture-retentive cooling gel laminate being supported on the support sheet.

66. A moisture-retentive cooling plaster as set forth in claim 65, wherein the air-permeable support sheet contains an endothermally water-dissolvable compound.

67. A moisture-retentive cooling plaster as set forth claim 66, wherein the laminate is formed into a planer layer having opposite surfaces on at least one of which is covered with a liner.

68. A moisture-retentive cooling plaster comprising a moisture-retentive cooling gel, said cooling gel comprising: a water-retentive matrix of a water-soluble polymer, said matrix having a water content of not lower than 40 wt %; and a water-absorbing polymer filler dispersed in the water-retentive matrix, at least one of the water-absorbing polymer filler being exposed on a surface of the water-retentive matrix; and an air-permeable support sheet, the moisture-retentive cooling gel being supported on the support sheet.

69. A moisture-retentive cooling plaster as set forth in claim 68, wherein the air-permeable support sheet contains an endothermally water-dissolvable compound.

70. A moisture-retentive cooling plaster as set forth in claim 68, wherein the gel is formed into a planer layer having opposite surfaces on at least one of which is covered with a liner.

71. A moisture-retentive cooling gel laminate comprising a mesh sheet as plurality of layers of a moisture-retentive cooling gel, said cooling gel comprising: a water-retentive matrix of a water-soluble polymer, said matrix having a water content of not lower than 40 wt %; and a water-absorbing polymer filler and fibers dispersed in the water-retentive matrix, the fibers having a hydrophilic property at least at surfaces thereof, at least some of the water-absorbing polymer filler and the fibers being exposed on a surface of the water-retentive matrix; the plurality of gel layers being stacked one on another with the mesh sheet interposed therebetween.

72. A moisture-retentive cooling gel laminate as set forth in claim 71, wherein the mesh sheet retains an endothermally water-dissolvable compound.

73. A moisture-retentive cooling gel laminate as set forth in claim 71, wherein the mesh sheet consists of a fibrous water-absorbing polymer.

74. A moisture-retentive cooling gel laminate as set forth in claim 71, wherein the water-absorbing polymer filler contains at least one compound selected from the group consisting of a water-soluble pharmacological active ingredient, a perfume and a deodorant.

75. A moisture-retentive cooling gel laminate as set forth in claim 71, which is formed into a planer layer having opposite surfaces on at least one of which is covered with a liner.

76. A moisture-retentive cooling plaster comprising a moisture-retentive cooling gel laminate as recited in claim 71 and an air-permeable support sheet, the moisture-retentive cooling gel laminate being supported on the support sheet.

77. A moisture-retentive cooling plaster as set forth in claim 76, wherein the air-permeable support sheet contains an endothermally water-dissolvable compound.

78. A moisture-retentive cooling plaster as set forth in claim 76, wherein the laminate is formed into a planer layer having opposite surfaces on at least one of which is covered with a liner.

79. A moisture-retentive cooling gel laminate comprising a mesh sheet, a layer of a moisture-retentive cooling gel, said cooling gel comprising: a water-retentive matrix of a water-soluble polymer, said matrix having a water content of not lower than 40 wt %; and a water-absorbing polymer filler and fibers dispersed in the water-retentive matrix; the fibers having a hydrophilic property at least at surfaces thereof, at least some of the water-absorbing polymer filler and the fibers being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the mesh sheet interposed therebetween.

80. A moisture-retentive cooling gel laminate as set forth in claim 79, wherein the mesh sheet contains an endothermally water-dissolvable compound.

81. A moisture-retentive cooling gel laminate as set forth in claim 79, wherein the mesh sheet consists of a fibrous water-absorbing polymer.

82. A moisture-retentive cooling gel laminate as set forth in claim 79, wherein the water-absorbing polymer filler contains at least one compound selected from the group consisting of a water-soluble pharmacological active ingredient, a perfume and a deodorant.

83. A moisture-retentive cooling gel laminate as set forth in claim 79, which is formed into a planer layer having opposite surfaces on at least one of which is covered with a liner.

84. A moisture-retentive cooling plaster comprising a moisture-retentive cooling gel laminate as recited in claim 79, an air-permeable support sheet, the moisture-retentive cooling gel laminate being supported on the support sheet.

85. A moisture-retentive cooling plaster as set forth in claim 84, wherein the air-permeable support sheet retains an endothermally water-dissolvable compound.

86. A moisture-retentive cooling plaster as set forth in claim 84, wherein the laminate is formed into a planer layer having opposite surfaces on at least one of which is covered with a liner.

87. A moisture-retentive cooling gel laminate comprising a porous sheet a plurality of layers of a moisture-retentive cooling gel, said cooling gel comprising: a water-retentive matrix of a water-soluble polymer, said matrix having a water content of not lower than 40 wt %; and a water-absorbing polymer filler and fibers dispersed in the water-retentive matrix, the fibers having a hydrophilic property at least at surfaces thereof, at least some of the water-absorbing polymer filler and the fibers being exposed on a surface of the water-retentive matrix; the plurality of gel layers being stacked one on another with the porous sheet interposed therebetween.

88. A moisture-retentive cooling gel laminate as set forth in claim 87, wherein the porous sheet contains an endothermally water-dissolvable compound.

89. A moisture-retentive cooling gel laminate as set forth in claim 87, wherein the porous sheet consists of a polyurethane foam sheet containing open cells.

90. A moisture-retentive cooling gel laminate as set forth in claim 87, wherein the water-absorbing polymer filler contains at least one compound selected from the group consisting of a water-soluble pharmacological active ingredient, a perfume and a deodorant.

91. A moisture-retentive cooling gel laminate as set forth in claim 87, which is formed into a planer layer having opposite surfaces on at least one of which is covered with a liner.

92. A moisture-retentive plaster comprising a moisture-retentive cooling gel laminate as recited in claim 87 an air-permeable support sheet, the moisture-retentive cooling gel laminate being supported on the support sheet.

93. A moisture-retentive cooling plaster as set forth in claim 92, wherein the air-permeable support sheet contains an endothermally water-dissolvable compound.

94. A moisture-retentive cooling plaster as set forth in claim 92, wherein the laminate is formed into a planer layer having opposite surfaces on at least one of which is covered with a liner.

95. A moisture-retentive cooling gel laminate comprising a porous sheet, a layer of a moisture-retentive cooling gel, said cooling gel comprising: a water-retentive matrix of a water-soluble polymer, said matrix having a water content of not lower than 40 wt %; and a water-absorbing polymer filler and fibers dispersed in the water-retentive matrix, the fibers having a hydrophilic property at least at surfaces thereof, at least some of the water-absorbing polymer filler and the fibers being exposed on a surface of the water-retentive matrix; and a layer of an endothermic gel, the endothermic gel comprising a water-retentive matrix of a water-soluble polymer having a water content of not lower than 40 wt % and an endothermally water-dissolvable compound, the moisture-retentive cooling gel layer and the endothermic gel layer being stacked one on the other with the porous sheet interposed therebetween.

96. A moisture-retentive cooling gel laminate as set forth in claim 95, wherein the porous sheet contains an endothermally water-dissolvable compound.

97. A moisture-retentive cooling gel laminate as set forth in claim 95, wherein the porous sheet consists of a polyurethane foam sheet containing open cells.

98. A moisture-retentive cooling gel laminate as set forth in claim 95, wherein the water-absorbing polymer filler contains at least one compound selected from the group consisting of a water-soluble pharmacological active ingredient, a perfume and a deodorant.

99. A moisture-retentive cooling gel laminate as set forth in claim 95, which is formed into a planer layer having opposite surfaces on at least one of which is covered with a liner.

100. A moisture-retentive cooling plaster comprising a moisture-retentive cooling gel laminate as recited in claim

95 and an air-permeable support sheet, the moisture-retentive cooling gel laminate being supported on the support sheet.

101. A moisture-retentive cooling plaster as set forth in claim 100, wherein the air-permeable support sheet contains an endothermally water-dissolvable compound.

102. A moisture-retentive cooling plaster as set forth in claim 101, wherein the laminate is formed into a planer layer having opposite surfaces on at least one of which is covered with a liner.

103. A moisture-retentive cooling plaster comprising a moisture-retentive cooling gel, said cooling gel comprising: a water-retentive matrix of a water-soluble polymer, said matrix having a water content of not lower than 40 wt %; and a water-absorbing polymer filler and fibers dispersed in the water-retentive matrix, the fibers having a hydrophilic property at least at surfaces thereof, at least some of the water-absorbing polymer filler and the fibers being exposed on a surface of the water-retentive matrix; and an air-permeable support sheet, the moisture-retentive cooling gel being supported on the support sheet.

104. A moisture-retentive cooling plaster as set forth in claim 103, wherein the air-permeable support sheet contains an endothermally water-dissolvable compound.

105. A moisture-retentive cooling plaster as set forth in claim 103, wherein the gel is formed into a planer layer having opposite surfaces on at least one of which is covered with a liner.

* * * * *